United States Patent
Uehara Matsuoka

(10) Patent No.: US 11,617,706 B2
(45) Date of Patent: Apr. 4, 2023

(54) HAIR CONDITIONING COMPOSITION FREE OF FATTY ALCOHOL

(71) Applicant: The Procter & Gamble Company, Cincinnati, OH (US)

(72) Inventor: Nobuaki Uehara Matsuoka, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 19 days.

(21) Appl. No.: 17/350,079

(22) Filed: Jun. 17, 2021

(65) Prior Publication Data

US 2021/0401706 A1     Dec. 30, 2021

Related U.S. Application Data

(60) Provisional application No. 63/045,428, filed on Jun. 29, 2020.

(51) Int. Cl.

| | | |
|---|---|---|
| *A61Q 5/12* | (2006.01) | |
| *A61K 8/04* | (2006.01) | |
| *A61K 8/06* | (2006.01) | |
| *A61K 8/34* | (2006.01) | |
| *A61K 8/36* | (2006.01) | |
| *A61K 8/44* | (2006.01) | |
| *A61K 8/49* | (2006.01) | |
| *A61K 8/02* | (2006.01) | |
| *A61K 8/35* | (2006.01) | |
| *A61K 8/37* | (2006.01) | |
| *A61Q 17/00* | (2006.01) | |

(52) U.S. Cl.
CPC ............ *A61K 8/042* (2013.01); *A61K 8/0233* (2013.01); *A61K 8/06* (2013.01); *A61K 8/068* (2013.01); *A61K 8/342* (2013.01); *A61K 8/345* (2013.01); *A61K 8/35* (2013.01); *A61K 8/361* (2013.01); *A61K 8/375* (2013.01); *A61K 8/44* (2013.01); *A61K 8/4946* (2013.01); *A61Q 5/12* (2013.01); *A61Q 17/005* (2013.01); *A61K 2800/21* (2013.01); *A61K 2800/30* (2013.01); *A61K 2800/33* (2013.01); *A61K 2800/34* (2013.01); *A61K 2800/412* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 4,725,433 A * | 2/1988 | Matravers | A61K 8/731 424/70.13 |
| 5,968,492 A | 10/1999 | Noguchi et al. | |
| 6,432,420 B2 | 8/2002 | Ellis et al. | |
| 9,572,769 B2 | 2/2017 | Park et al. | |
| 9,642,788 B2 | 5/2017 | Marsh et al. | |
| 2001/0008631 A1 | 7/2001 | Ellis et al. | |
| 2006/0058205 A1* | 3/2006 | Ainger | A61Q 5/12 510/121 |
| 2006/0078528 A1* | 4/2006 | Yang | A61K 8/891 424/70.27 |
| 2009/0071493 A1* | 3/2009 | Nguyen | A61K 8/736 132/202 |
| 2010/0330004 A1 | 12/2010 | Burgo | |
| 2014/0335036 A1 | 11/2014 | Marsh et al. | |
| 2016/0015615 A1 | 1/2016 | Mann et al. | |
| 2016/0175209 A1 | 6/2016 | Walker et al. | |
| 2018/0333494 A1 | 11/2018 | Lane et al. | |
| 2019/0282478 A1 | 9/2019 | Pesaro et al. | |
| 2020/0056118 A1 | 2/2020 | Schulze et al. | |

FOREIGN PATENT DOCUMENTS

| | | |
|---|---|---|
| CA | 2330943 C | 12/2009 |
| CN | 102178612 A | 9/2011 |
| CN | 102988195 A | 3/2013 |
| CN | 106551799 A | 4/2017 |
| CN | 106619149 A | 5/2017 |
| CN | 106726640 A | 5/2017 |
| CN | 106726641 A | 5/2017 |
| CN | 106726642 A | 5/2017 |
| CN | 106726643 A | 5/2017 |
| EP | 0964673 B1 | 10/2003 |
| EP | 1752193 A1 | 2/2007 |
| EP | 2774481 A1 | 9/2014 |
| FR | 2730931 A1 | 8/1996 |
| JP | 2003238329 A | 8/2003 |
| JP | 5657191 B2 | 12/2014 |
| JP | 5969793 B2 | 7/2016 |
| WO | 0051555 A1 | 9/2000 |
| WO | 0051556 A1 | 9/2000 |
| WO | 2007093271 A2 | 8/2007 |
| WO | 2020043269 A1 | 3/2020 |
| WO | 2020182318 A1 | 9/2020 |

OTHER PUBLICATIONS

PCT Search Report and Written Opinion for PCT/US2021 /037823 dated Nov. 2, 2021, 10 pages.
Anna Herman: "Antimicrobial Ingredients as Preservative Booster and Components of Self-Preserving Cosmetic Products", Current Microbiology, vol. 76, No. 6, Apr. 12, 2018 , pp. 744-754, XP055619588, New York, ISSN: 0343-8651, DOI: 10.1007/s00284.
Anonymous: "What is Pentylene Glycol?", Jul. 27, 2019, XP055856110, Retrieved from the Internet:URL:https://nayaglow.com/blogs/news/what-is-pentylene-glycol[retrieved on Oct. 28, 2021], 10 pages.
Ayako Hirai et al: "Effects of 1-arginine on aggregates of fatty-acid/potassium soap in the aqueous media", Colloid and Polymer Science, Springer, Berlin, DE, vol. 284, No. 5, Feb. 1, 2006 (Feb. 1, 2006), pp. 520-528, XP019340539, ISSN: 1435-1536, DOI: 10.1007/S00396-005-1423-1.
All Office Actions; U.S. Appl. No. 17/350,069, filed Jun. 17, 2021.
All Office Actions; U.S. Appl. No. 17/350,088, filed Jun. 17, 2021.

(Continued)

*Primary Examiner* — Jyothsna A Venkat
(74) *Attorney, Agent, or Firm* — Kathleen Y. Carter

(57) ABSTRACT

A hair conditioner composition comprising arginine, a fatty acid having a C16 to C22 alkyl chain, and an aqueous carrier, all of which form a gel structure, and wherein the composition is free of a fatty alcohol.

11 Claims, No Drawings

(56) References Cited

OTHER PUBLICATIONS

U.S. Appl. No. 17/350,069, filed Jun. 17, 2021, to first inventor Nobuaki Uehara Matsuoka et al.
U.S. Appl. No. 17/350,088, filed Jun. 17, 2021, to first inventor Nobuaki Uehara Matsuoka et al.

* cited by examiner

HAIR CONDITIONING COMPOSITION FREE OF FATTY ALCOHOL

FIELD OF THE INVENTION

The present invention relates to a hair conditioning composition comprising arginine, a fatty acid, and aqueous carrier, all of which form a gel structure, wherein the composition does not comprise a fatty alcohol.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. For example, some cationic surfactants, when used together with some high melting point fatty compounds and an aqueous carrier, are believed to provide a gel structure or a lamellar gel network matrix with a $L_\beta$ phase, which is suitable for providing a variety of conditioning benefits such as a slippery feel during the application to wet hair, softness, and a moisturized feel on dry hair.

But some consumers would prefer products that do not have cationic surfactant molecules. More broadly, some consumers would prefer products with very simple formulations, meaning only a small number of ingredients, or ingredients that are all natural, or ingredients that do not involve heavy chemical processing.

Thus, there is a continuing need to formulate hair care compositions with a minimal number of natural ingredients that can still form a gel structure in formulation and deliver the consumer-desired benefits.

None of the existing art provides all of the advantages and benefits of the present invention, including performance, cost, safety, and being environmental-friendly.

SUMMARY OF THE INVENTION

The present invention is directed to a hair conditioning composition comprising arginine, a fatty acid having C16 to C22 alkyl chains, and an aqueous carrier, all of which form a gel structure in formulation, and wherein the composition is free of a fatty alcohol.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Q.S. herein means up to 100%.

Composition

The hair conditioning composition of the present invention comprising:
  a) arginine;
  b) a fatty acid having C16 to C22 alkyl chains; and
  c) an aqueous carrier;
    wherein a) through c) form a gel structure;
    and wherein the composition is free of a fatty alcohol.

The objective of the invention is to provide stable conditioner compositions containing a gel structure and having an acceptable application feel and dry look and feel benefits. The combination of a C16 to C22 fatty acid and arginine, along with an aqueous carrier enables the preparation of structures that allow a good rheology profile and that provide good phase stability and application feel. The gel structure is robust enough to provide compositional stability. The gel structure and the composition further deliver dry conditioning benefits such as hair manageability, frizz control, and volume.

A typical hair conditioner composition comprises a structurant, such as a fatty alcohol, a feel/rheology modifier polymer, a conditioning oil and agent, perfumes/colorants, plus a cationic surfactant. As consumers become more interested in products comprising fewer ingredients, and only natural and gentle ingredients, each of these hair conditioner components is examined for how consumer-perceived natural and gentle ingredients can make up the composition, while still providing the performance and benefits that consumers expect. One area that may be modified is the surfactant. Rather than use a cationic surfactant molecule, the present inventors have formulated hair conditioner compositions comprising specific combinations of fatty acids and the basic amino acid arginine. This combination provides a minimal number of ingredients (a total of three including water) that form a gel structure that provides hair conditioning with the right rheological property for application. The base chassis of the inventive compositions can be free of a cationic surfactant and free of a fatty alcohol. While using a fatty alcohol can require a chemical/metal catalysis at extreme process conditions, the compositions of the present invention require only hydrolysis for the fatty acid and fermentation for arginine. Thus, the inventive compositions provide natural, sustainably sourced, environmentally-friendly, and gentle ingredients that allow flexibility in molecular design and the supply chain, while still meeting performance, cost, safety, and environmental-friendly criteria.

Gel Structure

The compositions of the present invention comprise a gel structure or gel network, in some cases a lamellar gel network matrix with a $L_\beta$ phase. The gel structure is suitable for providing various conditioning benefits, such as slippery feel during the application to wet hair and softness and moisturized feel on dry hair.

The gel structure of the inventive hair conditioner compositions comprises a surfactant that comprises arginine and a longer alkyl chain of a fatty acid that contains C16-C22 as its major chain length.

The composition may comprise from about 0.01% to about 40% of arginine, by weight of the hair conditioner composition. In some embodiments, the amount of arginine may be from about 0.01% to about 40%, from about 0.1% to about 20%, from about 0.2% to about 15%, by weight of the hair care conditioner composition.

The arginine of the present invention may be combined with a fatty acid at certain pH (greater than 4.5) and processing conditions to form a gel structure. The composition may comprise from about 0.02% to about 40% of the fatty acid, by weight of the hair conditioner composition. In some embodiments, the amount of the fatty acid may be from about 0.02% to about 40%, from about 0.05% to about 20%, from about 0.1% to about 15%, by weight of the hair conditioner composition. The fatty acid may comprise saturated and/or unsaturated fatty acids. In some embodiments, the fatty acid may comprise from about 0.05% to about 5% of unsaturated fatty acid, by weight of the hair conditioner composition. The fatty acid may have C16-C22 alkyl chains, or in some cases C18-C22 alkyl chains as the main components. The saturated fatty acid may include, but is not limited to, stearic acid, palmitic acid, behenic acid, and combinations thereof. The unsaturated fatty acid may include, but is not limited to, rapeseed acid, oleic acid, linoleic acid, and combinations thereof. The hair conditioner compositions may comprise at least about 60% of an aqueous carrier, by weight of said hair conditioner composition, and in some embodiments at least about 80%.

The inventive compositions herein may form a lamellar gel network matrix with a $L_\beta$ phase that comprises a fatty acid, arginine, and an aqueous carrier. In general, the mixture of arginine and the fatty acid, along with an aqueous carrier, may have a pH of at least about 4.5. The ratio of basic amino acid arginine to the fatty acid may be from about 1:100 to about 40:1, from about 1:20 to about 30:1, from about 1:10 to about 20:1.

The compositions of the present invention may be substantively free of ceramide. The compositions of the present invention may be substantively free of cholesterol. And the compositions of the present invention may be substantively free of a gel network made of only non-ionic surfactant. The compositions of the present invention may also be free of, or substantially free of, a fatty alcohol and/or a cationic surfactant.

Aqueous Carrier

The conditioning composition of the present invention comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 70% to about 90% water.

Silicone Compound

The compositions of the present invention may, or may not, contain a silicone compound. It is believed that the silicone compound can provide smoothness and softness on dry hair. The silicone compounds herein can be used at levels by weight of the composition of preferably from about 0.1% to about 20%, more preferably from about 0.5% to about 10%, still more preferably from about 1% to about 8%.

Preferably, the silicone compounds have an average particle size of from about 1 micron to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (I):

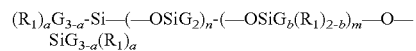

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$$A^-$; —N($R_2$)$CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is N(CH3)2 or —NH2, more preferably —NH2. Another highly preferred amino silicones are those corresponding to formula (I) wherein m=0, a=1, q=3, G=methyl, n is preferably from about 400 to about 600, more preferably about 500; and L is —N(CH3)2 or —$NH_2$, more preferably —$NH_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning. Some embodiments may include Silicone Quaternium-26.

The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 20%, preferably up to about 10% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; and sequestering agents, such as disodium ethylenediamine tetra-acetate; ultraviolet and infrared screening and absorbing agents such as benzophenones; and antidandruff agents such as zinc pyrithione.

Low Melting Point Oil

The compositions may comprise one or more conditioning oils. Low melting point oils useful herein are those having a melting point of less than 25° C. The low melting point oil useful herein is selected from the group consisting of: hydrocarbon having from 10 to about 40 carbon atoms; ester oils such as pentaerythritol ester oils including pentaerythritol tetraisostearate, trimethylol ester oils, citrate ester oils, and glyceryl ester oils; poly α-olefin oils such as polydecenes; and mixtures thereof. Additional oils may include triglycerides, such as caprylic capric triglyceride or vegetable oils such as coconut oil, soybean oil, rapeseed oil, cocoa butter, olive oil, palm oil, rice bran oil, and mixtures thereof.

In some embodiments, a conditioning oil may have a hydrophilic-lipophilic balance (HLB) of less than about 10. In some embodiments, the oil may be a mono, di, or tri ester or ether where the monomer units have a carbon chain of C2 to C16, preferably C4 to C10, or more preferably C6 to C8. In some embodiments, the oil may be a polyester with the hydrophobic monomer units (linear or branched) having carbon chains shorter than C16, preferably shorter than C12. Commercially available oil examples include, but are not limited to, Myritol 318 from BASF (caprylic/capric triglyceride), Plantasil Micro from BASF (dicaprylyl ether in emulsion form (Dicaprylyl Ether (and) Decyl Glucoside (and) Glyceryl Oleate)); or Citropol 1A from P2 science (Polycitronellol Acetate), Product Forms The conditioning compositions of the present invention can be in the form of rinse-off products or leave-on products and can be formulated in a wide variety of product forms, including but not limited to pastes, creams, gels, emulsions, mousses, and sprays. The conditioning composition of the present invention is especially suitable for a rinse-off hair conditioner or for a no-rinse hair conditioner.

Method of Use

The conditioning composition of the present invention is preferably used for a method of conditioning hair, the method comprising following steps:

(i) after shampooing hair, applying to the hair an effective amount of the conditioning composition for conditioning the hair; and (ii) optionally, then rinsing the hair.

Effective amount herein is, for example, from about 0.1 ml to about 2 ml per 10 g of hair, preferably from about 0.2 ml to about 1.5 ml per 10 g of hair.

The conditioning composition of the present invention provides improved conditioning benefits, especially improved wet conditioning benefits after rinsing and improved dry conditioning, while maintaining wet conditioning benefit before rinsing. The conditioning composition of the present invention may also provide improved product appearance to consumer. Thus, a reduced dosage of the conditioning composition of the present invention may provide the same level of conditioning benefits as those of a full dosage of conventional conditioner compositions. Such reduced dosage herein is, for example, from about 0.3 ml to about 0.7 ml per 10 g of hair.

Method of Manufacturing

The present invention is also directed to a method of manufacturing a hair conditioning composition as follows: A method of making the hair conditioner composition comprising:
 a. arginine;
 b. a fatty acid having a C16 to C22 alkyl chain; and
 c. an aqueous carrier;
said method comprising the following steps:
a) Add water that is at a temperature higher than the temperature of the melting point of the fatty acid (about 80° C.-90° C.);
b) Add arginine and fatty acid into heated water and wait until the mixture is dissolved and dispersed homogenously; and
c) Cool the mixture below the phase transition temperature to form a gel structure.

The method may further comprise the steps of adding additional ingredients such as silicone or oil compounds, perfumes, preservatives, esthetics if included, to the gel structure. The inventive conditioning compositions of the present invention can be prepared by any conventional method well known in the art.

The pH of the finished product and of the composition during the making process after the cooling down step may be at least 4.5.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Table 1 shows two inventive compositions along with four comparative examples. Inventive Example 1 has arginine and stearic acid (C16/C18 chain) in an aqueous carrier, and Inventive Example 2 has arginine and behenic acid (C22 chain) in an aqueous carrier. Both Inventive Examples form stable products, have DSC peaks greater than 30 (indicating a gel structure), and have acceptable dry conditioning. In contrast, arginine with C12 fatty acid (Comparative Example 3) and histidine with C12, 16/18, or 22 fatty acid (Comparative Examples 4, 5, and 6, respectively) exhibit phase separation, which indicates that the gel structure/matrix cannot be formed.

TABLE 1

|  | Inv. Ex. 1 | Inv. Ex. 2 | Comp. Ex. 3 | Comp. Ex. 4 | Comp. Ex. 5 | Comp. Ex. 6 |
| --- | --- | --- | --- | --- | --- | --- |
| Description | Inventive Example 1 Arginine: C18 Stearic Acid | Inventive Example 2 Arginine: C22 Behenic Acid | Arginine: Lower Carbon Chain C12 Lauric Acid | Histidine: Lower Carbon Chain C12 Lauric Acid | Histidine: C18 Stearic Acid | Histidine: C22 Behenic Acid |
| L-Arginine | 0.65 | 0.65 | 0.65 | — | — | — |
| Histidine | — | — | — | 0.65 | 0.65 | 0.65 |
| Lauric Acid | — | — | 6.51 | 6.51 | — | — |
| Stearic Acid* | 6.51 | — | — | — | 6.51 | — |
| Behenic Acid | — | 6.51 | — | — | — | 6.51 |
| Oleyl Alcohol | — | — | — | — | — | — |
| Water | Q.S, | Q.S, | Q.S, | Q.S, | Q.S, | Q.S, |
| Rheology Shear Stress at 950 S-1 (Pa) | 61 | 112 | NA | NA | NA | NA |
| Rheology G' (Pa) | 5930 | 100 | NA | NA | NA | NA |
| Rheology G" (Pa) | 1548 | 38 | NA | NA | NA | NA |
| Product Stability | Stable | Stable | Phase Separation | Phase Separation | Phase Separation | Phase Separation |
| DSC Peak >30 C | Yes | Yes | NA | NA | NA | NA |
| Dry Conditioning | Acceptable | Acceptable | NA | NA | NA | NA |

*It has chain distribution of C16/C18 at around 50/50.

Table 2 shows additional inventive examples comprising silicone and/or oil.

TABLE 2

|  | Ex. 7 Addition of Oil | Ex. 8 Addition of Silicone | Ex.9 Addition of Oil and Silicone |
| --- | --- | --- | --- |
| L-Arginine | 0.22 | 0.65 | 13.64 |
| Behenic Acid | 2.17 | 6.51 | 1.36 |
| Polycitronellol Acetate | 5.00 | — | 1.0 |
| Caprylic Capric Triglyceride | — | — | — |

TABLE 2-continued

|  | Ex. 7 Addition of Oil | Ex. 8 Addition of Silicone | Ex.9 Addition of Oil and Silicone |
|---|---|---|---|
| Dimethicone | — | 3.0 | 2.0 |
| Bisaminoprotpyl dimethicone | — | — | 0.5 |
| Water | Q.S, | Q.S, | Q.S, |
| Dry Conditioning | Acceptable | Acceptable | Acceptable |

Test Methods

1. Dry Expert Sensory Method

This is expert sensory panel test method uses three highly expert sensory panel to evaluate specific attribute during dry stage hair treatment. The treatment protocol for the hair treatment is stated as follow:
  a. Rinse 20 g of hair switches with water and squeeze water out from top to bottom once.
  b. 1 ml conditioner was applied front and 1 ml conditioner was applied back.
  c. Lather the product 30 strokes for 30 seconds on hair switch.
  d. The hair was then rinse for 15 seconds front and 15 seconds back. and squeeze water out from top to bottom once.
  e. Leave overnight to dry The sensory attribute evaluated during this method is notated as "Dry Conditioning" in the Example tables. Panellist evaluated during the dry stage the smooth surface feel of the hair and was asked to find it either "Acceptable" or "Not Acceptable" (as conditioning feel).

2. DSC Analysis Method

The differential scanning calorimetry (DSC) is a convenient tool as it gives the phase transition (melting or freezing) temperature of formed structure, as well as the thermal energy of melting and freezing. The procedure method comprising the following steps:
1. Equilibrate 0.00° C.
2. Ramp 5.00° C./min to 90.00° C.
3. Isothermal 5.0 min
4. Ramp 5.00° C./min to 0.00° C.
5. Isothermal 5.0 min The description test for DSC Peak >30° C.: The DSC graph at Ramp 5.00° C./min to 90.00° C. will gives the melting phase transition temperature of formed structure. If a peak is observed higher than 30° C., then it will be stated as Yes.

3. Product Stability Visual Assessment

Stability is the visual assessment to ensure the product is consistently stable over a specific period. The composition of product was placed in three different condition—5° C., 25° C. and 40° C. The assessment will be taken at different interval:
1) Stable as made
2) Stable after one week
3) Stable after 3 months (25° C.)

The description test for Product Stability: If the visual assessment of the product is no phase-separation at all of 1), 2) and 3) conditions, it is stated as "Stable". If the visual assessment of the product exhibits phase separation at 1), 2) or 3), it is stated as "Phase Separation".

4. Rheology Method

Rheology is used to evaluate and characterize product samples. The two key rheology methods identified are mentioned below:

Shear Stress at 950 $s^{-1}$ via flow curve: This is the method to ramp up shear rate logarithmically from 0.1 to 1000 $s^{-1}$ in 1 min using a cone & plate geometry, and to read the shear stress value σ (Pa) at shear rate 950 $s^{-1}$.

Oscillatory Measurement G'/G": This is the Oscillatory stress method where it ramps from 0.1 to 100 Pa to measure storage modulus, G' and loss modulus, G" to give viscoelasticity information of "resting" state of sample, and the yield stress value σ (Pa), which is the stress required to permanently deform (starts to flow). The acceptable rheology range for shear stress is from 5 Pa until 1500 Pa. As for oscillatory measurement, the range for storage modulus, G' is from 30 Pa until 45000 Pa, and loss modulus, G" is from 10 Pa until 20000 Pa.

EXAMPLES/COMBINATIONS

A. A hair conditioner composition comprising:
  a) arginine;
  b) a fatty acid having C16 to C22 alkyl chains; and
  c) an aqueous carrier;
  wherein a) through c) form a gel structure;
  and wherein the composition is free of a fatty alcohol.

B. The composition of paragraph A, wherein the composition is free of a cationic surfactant molecule.

C. The composition of any one of paragraphs A or B, wherein the composition is free of silicone.

D. The composition of any one of paragraphs A to C, wherein the mixture of a, b, and c have a pH of at least about 4.5.

E. The composition of any one of paragraphs A to D, wherein the hair conditioner composition comprises from about 0.01% to about 40% of arginine, by weight of the hair conditioner composition.

F. The composition of any one of paragraphs A to E, wherein the hair conditioner composition comprises from about 0.02% to about 40% of fatty acids, by weight of the hair conditioner composition.

G. The composition of any one of paragraphs A to F, wherein the fatty acid comprises saturated and unsaturated fatty acids.

H. The composition of any one of paragraphs A to G, wherein the ratio of a to b is from about 1:100 to about 40:1.

I. The composition of any one of paragraphs A to H, wherein the fatty acid comprises from about 0.05% to about 5% of unsaturated fatty acid, by weight of the hair conditioner composition.

J. The composition of any one of paragraphs A to I, wherein the composition further comprises conditioning oils.

K. The composition of paragraph J, wherein the conditioning oil is a non-silicone.

L. The composition of any one of paragraph J or K, wherein the conditioning oils are in preformed emulsion form, with a particle size at most about 500 nm.

M. The composition of any one of paragraph J to L, wherein the conditioning oils have an HLB of less than about 10.

N. The composition of any one of paragraph A to M, wherein the gel structure is a lamellar gel network matrix with a $L_\beta$ phase.

O. A method of making a hair conditioner composition, comprising the following steps:
  a) heat water to between 80° C. and 90° C.;
  b) add arginine and fatty acid into the heated water and wait until the mixture is dissolved and dispersed homogenously; and
  c) cool the mixture below the phase transition temperature to form a gel structure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioner composition comprising:
    a) arginine;
    b) a fatty acid having C16 to C22 alkyl chains; and
    c) an aqueous carrier;
    wherein a) through c) form a gel structure;
    and wherein the composition is free of a fatty alcohol and wherein the composition is free of cationic surfactant, and wherein the composition is free of silicone, and wherein the composition is free of ceramide, and wherein the composition is free of cholesterol, and wherein the composition is free of non-ionic surfactant,
    wherein the ratio of a to b is from about 1:100 to about 40:1.

2. The hair conditioner composition of claim 1, wherein the mixture of a, b, and c have a pH of at least about 4.5.

3. The hair conditioner composition of claim 1, wherein the hair conditioner composition comprises from about 0.01% to about 40% of arginine, by weight of the hair conditioner composition.

4. The hair conditioner composition of claim 1, wherein the hair conditioner composition comprises from about 0.02% to about 40% of fatty acid having C16 to C22 alkyl chains, by weight of the hair conditioner composition.

5. The hair conditioner composition of claim 1, wherein the fatty acid having C16 to C22 alkyl chains comprises saturated and unsaturated fatty acids.

6. The hair conditioner of claim 1, wherein the fatty acid having C16 to C22 alkyl chains comprises from about 0.05% to about 5% of unsaturated fatty acid, by weight of the hair conditioner composition.

7. The hair conditioner of claim 1, wherein the composition further comprises a conditioning oil.

8. The hair conditioner of claim 7, wherein the conditioning oil is a non-silicone.

9. The hair conditioner of claim 7, wherein the conditioning oils are in preformed emulsion form, with a particle size at most about 500 nm.

10. The hair conditioner of claim 7, wherein the conditioning oils have an HLB of less than about 10.

11. The hair conditioner of claim 1, wherein the gel structure is a lamellar gel network matrix with a $L_\beta$ phase.

* * * * *